United States Patent
Cho et al.

(10) Patent No.: US 11,352,655 B2
(45) Date of Patent: Jun. 7, 2022

(54) **METHOD OF IDENTIFICATION OF METHICILLIN-RESISTANT *STAPHYLOCOCCUS AUREUS***

(71) Applicant: CHINA MEDICAL UNIVERSITY HOSPITAL, Taichung (TW)

(72) Inventors: Der-Yang Cho, Taichung (TW); Jiaxin Yu, Taichung (TW); Ni Tien, Taichung (TW); Chao-Jung Chen, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 17/170,912

(22) Filed: Feb. 9, 2021

(65) Prior Publication Data
US 2022/0064694 A1 Mar. 3, 2022

Related U.S. Application Data

(60) Provisional application No. 63/071,392, filed on Aug. 28, 2020.

(30) Foreign Application Priority Data

Nov. 3, 2020 (TW) ................. 109138304

(51) Int. Cl.
*C12Q 1/14* (2006.01)
*C07K 14/31* (2006.01)

(52) U.S. Cl.
CPC .............. *C12Q 1/14* (2013.01); *C07K 14/31* (2013.01); *G01N 2333/31* (2013.01)

(58) Field of Classification Search
None
See application file for complete search history.

(56) References Cited

FOREIGN PATENT DOCUMENTS

KR WO2020/122427 6/2020

OTHER PUBLICATIONS

Wang et al. 2018 (Application of a MALDI-TOF analysis platform (ClinProTools) for rapid and preliminary report of MRSA sequence types in Taiwan; PeerJ 6:e5784; DOI 10.7717/peerj.5784). (Year: 2018).*
Edwards et al. 2000 (Rapid discrimination between methicillin-sensitive and methicillin-resistant *Staphylococcus aureus* by intact cell mass spectrometry; The Pathological Society of Great Britain and Ireland; ISSN 0022-2615) (Year: 2000).*
Memo regarding Nucleic Acid and Peptide Claim Interpretations; dated Dec. 29, 2005: (Year: 2005).*
Diep et al., 2006 (Complete genome sequence of USA300, an epidemic clone of community-acquired methicillin-resistant *Staphylococcus aureus* Lancet 2006; 367: 731-39) (Year: 2006).*
Josten M et al, Analysis of the Matrix-Assisted Laser Desorption Ionization-Time of Flight Mass Spectrum of *Staphylococcus aureus* Identifies Mutations That Allow Differentiation of the Main Clonal Lineages, Journal of Clinical Microbiology, 2013, 51(6), pp. 1809-1817.
Sogawa K et al, Rapid Discrimination between Methicillin-Sensitive and Methicillin-Resistant *Staphylococcus aureus* Using MALDI-TOF Mass Spectrometry, Journal of Biocontrol Science, 2017, 22(3), pp. 163-169.

* cited by examiner

*Primary Examiner* — Mary Maille Lyons
(74) *Attorney, Agent, or Firm* — Hannah Tien

(57) ABSTRACT

Disclosed is a method for identifying methicillin-resistant *Staphylococcus aureus* through detection a mass signal at m/z of 6580-6600 in the MALDI-TOF mass spectrum. Also disclosed is a novel peptide biomarker, which consists of SEQ NO ID:5 and the use thereof for detection and/or identification of methicillin-resistant *Staphylococcus aureus*.

8 Claims, 20 Drawing Sheets
(2 of 20 Drawing Sheet(s) Filed in Color)
Specification includes a Sequence Listing.

Fig. 3
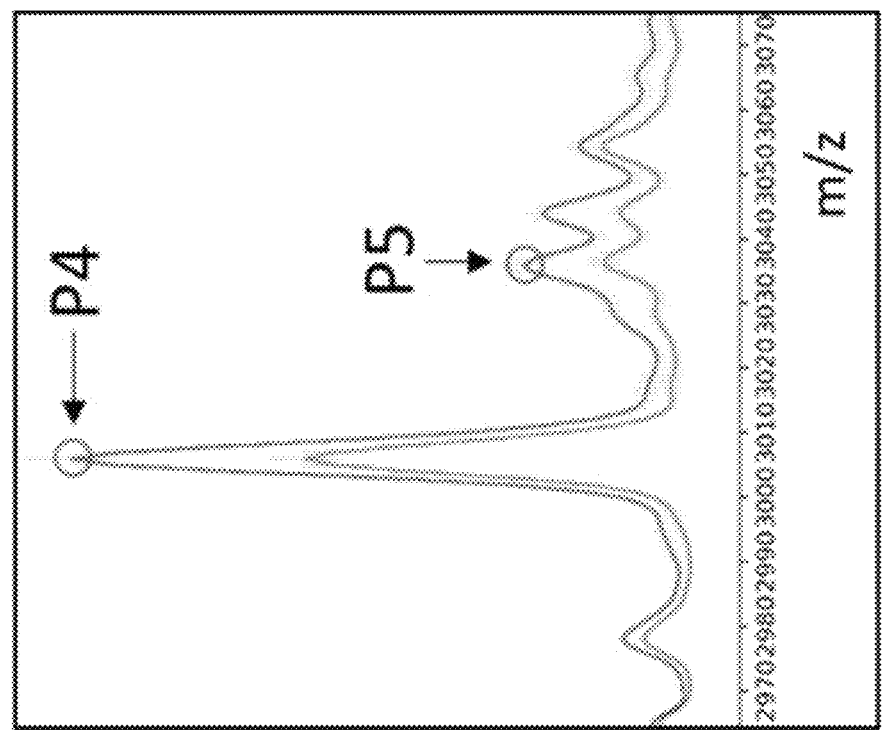
Fig. 3B
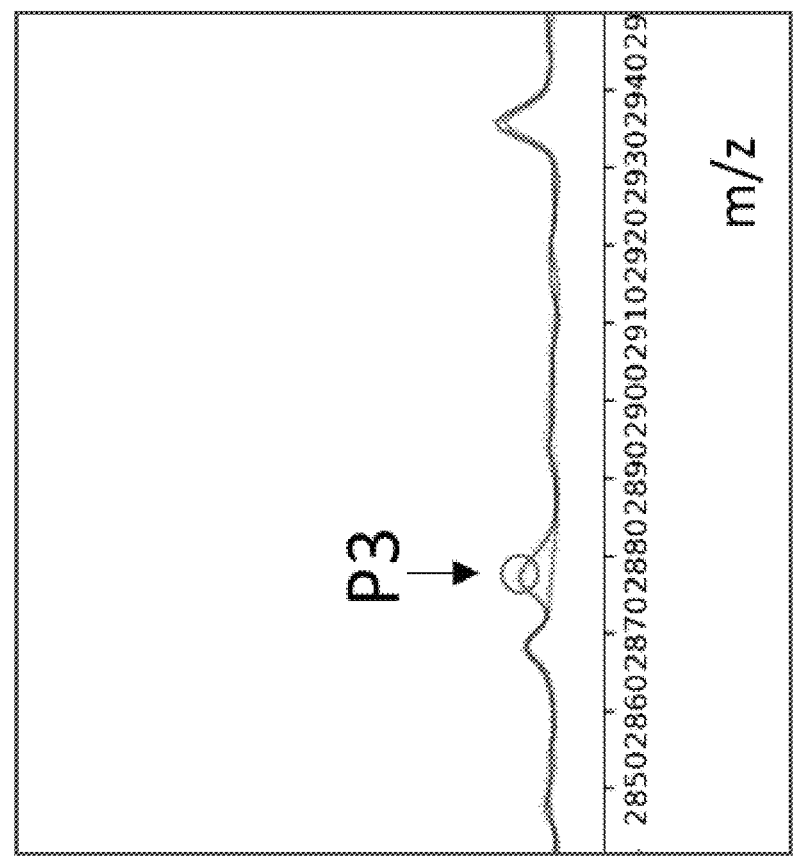
Fig. 3C

Fig. 11
Fig. 11A
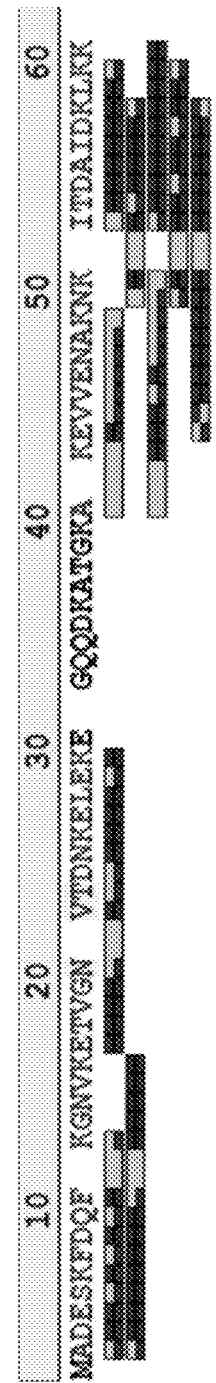
Trypsin digestion
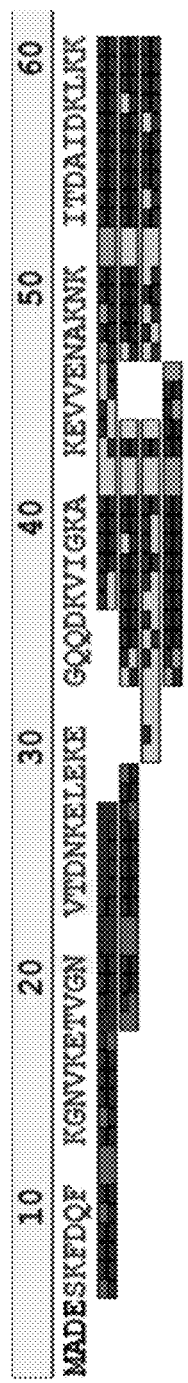
Glu-C digestion

| Accession | Protein | Scores | m/z meas. | z | MH+ meas. | Sequence | Range | Modifications |
|---|---|---|---|---|---|---|---|---|
| Y1582_STAA3 | UPF0337 protein SAUSA300_1582 | 158:152.7 (M:152.7) | 567.6577 | 3 | 1700.9584 | E.NAKNKITDAIDKLKK.- | 46-60 | Deamidated: 1 |
| Y1582_STAA3 | UPF0337 protein SAUSA300_1582 | 158:131.6 (M:131.6) | 567.3288 | 3 | 1699.9719 | E.NAKNKITDAIDKLKK.- | 46-60 | |
| Y1582_STAA3 | UPF0337 protein SAUSA300_1582 | 158:122.7 (M:122.7) | 567.6578 | 3 | 1700.9588 | E.NAKNKITDAIDKLKK.- | 46-60 | Deamidated: 4 |
| Y1582_STAA3 | UPF0337 protein SAUSA300_1582 | 158:99.1 (M:99.1) | 814.4373 | 2 | 1627.8674 | E.GQQDKVIGKAKEVVE.N | 31-45 | |
| Y1582_STAA3 | UPF0337 protein SAUSA300_1582 | 158:88.5 (M:88.5) | 650.8508 | 2 | 1300.6943 | E.GQQDKVIGKAKE.V | 31-42 | |
| Y1582_STAA3 | UPF0337 protein SAUSA300_1582 | 158:71.9 (M:71.9) | 713.8551 | 2 | 1426.7029 | E.SKFDDFKGNVKE.T | 5-16 | |
| Y1582_STAA3 | UPF0337 protein SAUSA300_1582 | 158:63.6 (M:63.6) | 538.7546 | 2 | 1076.5019 | E.TVGNVTDNKE.L | 17-26 | |
| Y1582_STAA3 | UPF0337 protein SAUSA300_1582 | 158:61.3 (M:61.3) | 659.8144 | 2 | 1318.6215 | E.TVGNVTDNKELE.K | 17-28 | |
| Y1582_STAA3 | UPF0337 protein SAUSA300_1582 | 158:59.9 (M:59.9) | 779.4154 | 2 | 1557.8235 | E.KEGQQDKVIGKAKE.V | 29-42 | |
| Y1582_STAA3 | UPF0337 protein SAUSA300_1582 | 158:35.2 (M:35.2) | 600.3589 | 2 | 1199.7105 | D.KVIGKAKEVVE.N | 35-45 | |

| Accession | Protein | Scores | m/z meas. | z | MH+ meas. | Sequence | Range | Modifications |
|---|---|---|---|---|---|---|---|---|
| Y1452_STAAN | UPF0337 protein SA1452 OS=Staphylococcus aureus (strain N315) | 112.8 (M:112.8) | 567.6513 | 3 | 1700.9392 | E.NAKNKTDADKLKK. | 46 - 60 | Deamidated: 1 |
| Y1452_STAAN | UPF0337 protein SA1452 OS=Staphylococcus aureus (strain N315) | 112.7 (M:112.7) | 850.4784 | 2 | 1699.9515 | E.NAKNKTDADKLKK. | 46 - 60 | |
| Y1452_STAAN | UPF0337 protein SA1452 OS=Staphylococcus aureus (strain N315) | 88.6 (M:88.6) | 850.9701 | 2 | 1700.9329 | E.NAKNKTDADKLKK. | 46 - 60 | Deamidated: 4 |
| Y1452_STAAN | UPF0337 protein SA1452 OS=Staphylococcus aureus (strain N315) | 78.0 (M:78.0) | 778.367 | 2 | 1555.7267 | D.ESKPDQPKGNVKET | 4 - 18 | |
| Y1452_STAAN | UPF0337 protein SA1452 OS=Staphylococcus aureus (strain N315) | 72.7 (M:72.7) | 713.8459 | 2 | 1426.6865 | E.SKPDQPKGNVKET | 5 - 16 | |
| Y1452_STAAN | UPF0337 protein SA1452 OS=Staphylococcus aureus (strain N315) | 52.6 (M:52.6) | 659.8147 | 2 | 1318.6221 | E.TVGNVTDNKELEK | 17 - 28 | |
| Y1452_STAAN | UPF0337 protein SA1452 OS=Staphylococcus aureus (strain N315) | 131.7 (M:31.7) | 794.3926 | 2 | 1587.778 | E.GQQDKATGKAKEVVE.N | 31 - 45 | |
| Y1452_STAAN | UPF0337 protein SA1452 OS=Staphylococcus aureus (strain N315) | 20.3 (M:20.5) | 660.3051 | 2 | 1319.6029 | E.TVGNVTDNKELEK | 17 - 28 | Deamidated: 8 |
| Y1452_STAAN | UPF0337 protein SA1452 OS=Staphylococcus aureus (strain N315) | 16.8 (M:16.8) | 630.808 | 2 | 1260.6087 | E.GQQDKATGKAKEV | 31 - 42 | |

SEQUENCE LISTING

<160> NUMBER OF SEQ ID NOS: 6

<210> SEQ ID NO 1
<211> LENGTH: 60
<212> TYPE: PRT
<213> ORGANISM: Staphylococcus aureus

<400> SEQUENCE: 1

Met Ala Asp Glu Ser Lys Phe Asp Gln Phe Lys Gly Asn Val Lys Glu
1               5                   10                  15

Thr Val Gly Asn Val Thr Asp Asn Lys Glu Leu Glu Lys Glu Gly Gln
            20                  25                  30

Gln Asp Lys Val Ile Gly Lys Ala Lys Glu Val Val Glu Asn Ala Lys
        35                  40                  45

Asn Lys Ile Thr Asp Ala Ile Asp Lys Leu Lys Lys
    50                  55                  60

<210> SEQ ID NO 2
<211> LENGTH: 59
<212> TYPE: PRT
<213> ORGANISM: Staphylococcus aureus

<400> SEQUENCE: 2

Ala Asp Glu Ser Lys Phe Asp Gln Phe Lys Gly Asn Val Lys Glu Thr
1               5                   10                  15

Val Gly Asn Val Thr Asp Asn Lys Glu Leu Glu Lys Glu Gly Gln Gln
            20                  25                  30

Asp Lys Val Ile Gly Lys Ala Lys Glu Val Val Glu Asn Ala Lys Asn
        35                  40                  45

Lys Ile Thr Asp Ala Ile Asp Lys Leu Lys Lys
    50                  55

<210> SEQ ID NO 3
<211> LENGTH: 60
<212> TYPE: PRT
<213> ORGANISM: Staphylococcus aureus

<400> SEQUENCE: 3

Met Ala Asp Glu Ser Lys Phe Asp Gln Phe Lys Gly Asn Val Lys Glu
1               5                   10                  15

Thr Val Gly Asn Val Thr Asp Asn Lys Glu Leu Glu Lys Glu Gly Gln
            20                  25                  30

Gln Asp Lys Ala Thr Gly Lys Ala Lys Glu Val Val Glu Asn Ala Lys
        35                  40                  45

Asn Lys Ile Thr Asp Ala Ile Asp Lys Leu Lys Lys
    50                  55                  60

<210> SEQ ID NO 4
<211> LENGTH: 59
<212> TYPE: PRT
<213> ORGANISM: Staphylococcus aureus

<400> SEQUENCE: 4

Ala Asp Glu Ser Lys Phe Asp Gln Phe Lys Gly Asn Val Lys Glu Thr
1               5                   10                  15

Val Gly Asn Val Thr Asp Asn Lys Glu Leu Glu Lys Glu Gly Gln Gln
            20                  25                  30

Asp Lys Ala Thr Gly Lys Ala Lys Glu Val Val Glu Asn Ala Lys Asn
        35                  40                  45

Lys Ile Thr Asp Ala Ile Asp Lys Leu Lys Lys
    50                  55

<210> SEQ ID NO 5
<211> LENGTH: 15
<212> TYPE: PRT
<213> ORGANISM: Staphylococcus aureus

<400> SEQUENCE: 5

Gly Gln Gln Asp Lys Val Ile Gly Lys Ala Lys Glu Val Val Glu
1               5                   10                  15

```
<210> SEQ ID NO 6
<211> LENGTH: 15
<212> TYPE: PRT
<213> ORGANISM: Staphylococcus aureus

<400> SEQUENCE: 6

Gly Gln Gln Asp Lys Ala Thr Gly Lys Ala Lys Glu Val Val Glu
1               5                   10                  15
```

METHOD OF IDENTIFICATION OF METHICILLIN-RESISTANT *STAPHYLOCOCCUS AUREUS*

CROSS-REFERENCES TO RELATED APPLICATIONS

This patent application claims the benefit of priority from U.S. Provisional Application Ser. No. 63/071,392 filed on Aug. 28, 2020 and Taiwan Application No. 109138304 filed on November 3, the content of each of which is incorporated herein by reference in their entirety. This patent application contains a Sequence Listing in a computer readable form, which is incorporated herein by reference.

TECHNICAL FIELD

The present invention relates to a method for identifying methicillin-resistant *Staphylococcus aureus* (MRSA), especially a method for distinguishing methicillin-resistant *Staphylococcus aureus* through a peptide biomarker.

BACKGROUND OF THE INVENTION

According to statistical results from 2000 to 2015, the annual antibiotic dose in 76 countries has increased from 21.1 billion doses of antibiotics to 34.8 billion doses of antibiotics, showing that the rate of antibiotic use has risen by 65% over the past 15 years. At the same time, the global human use of antibiotics has reached 42 billion doses in 2015 and it is estimated that by 2030, the daily antibiotic dose will increase by 200% to 128 billion doses per day. The statistical clinical results show that the abuse of antibiotics mainly occurs in the use of the wrong dose (19.9%), the frequency of use (18.9%), and the repeated treatment (18.1%). The wrong dose and repeated treatment may be the use of ineffective antibiotics by the antidrug bacteria.

The mechanisms of drug resistance in bacteria are controlled by drug resistance genes. Some of the drug resistance genes are inherently possessed by bacteria, and some are produced by passing plastids or jumpers to other bacteria. In an environment containing antibiotics, non-resistant bacteria will be eliminated, and the ones that survive are resistant bacteria. In other words, the abuse of antibiotics will cause more and more antibiotic-resistant bacteria, especially in areas where a lot of antibiotics are used, a significant increase in the proportion of resistant bacteria can be observed. For example, methicillin-resistance *Staphylococcus aureus* (MRSA) is a special bacterium that is resistant to methicillin and other antibiotics. This bacterium has extremely infectious, so it is classified as one of the super bacteria.

*Staphylococcus aureus* (*S. aureus*) can be found in human respiratory tract and on the skin. In general, *S. aureus* does not cause symptoms, but the bacteria occasionally cause diseases, including skin, wounds, urethra, lungs, blood infections and food poisoning. The use of antibiotics can effectively inhibit most of the infections of *Staphylococcus aureus*, but not inhibit the drug-resistant *Staphylococcus aureus*, which is resistant to methicillin and other antibiotics, such as oxacillin, oxacillin, penicillin, amoxicillin and cephalosporins. Therefore, the rapid and accurate diagnosis of drug-resistant *S. aureus* is urgently needed and extremely important for the subsequent use of antibiotics.

The diagnosis and treatment of microbial infections are completely different from cancer. Comprehensive judgment of clinical examination and immediate integration of clinical data are very important for the diagnosis and treatment of microbial infections. The infectious diseases such as sepsis, meningitis, pneumonia, urinary tract infection are all clinically manifested as acute symptoms. Therefore, it is necessary to correctly diagnose the pathogen of the infection and determine its antibiotic resistance in the shortest time. In clinical practice, when a patient has fever and other indicator of inflammatory reactions, indicating that the patient has the possibility of infection, the culture of microorganisms and empirical therapy of antibiotics are often carried out to control the patient's infection. Furthermore, the identification of microorganisms and antibiotic susceptibility tests can provide clinically correct use of antibiotics to improve patient survival. At the same time, it can also reduce the waste of medical expenses, the environmental pollution and destruction of antibiotics caused by the abuse of antibiotics.

The gold standard for clinical diagnosis of infectious diseases is mainly based on the results of laboratory microbial culture and identification. The current process is to inoculate the processed sample into a suitable medium for overnight culture after receiving the sample. After that, it still takes an additional 24 hours to perform traditional biochemical identification to determine the type of bacteria, and to conduct antibiotic drug susceptibility testing. Therefore, the complete microbial culture identification report needs to take 3-5 days to obtain. At present, to speed up the process of bacterial identification, many medical centers use matrix-assisted laser desorption/ionization time-of-flight mass spectrometry (MALDI-TOF MS) as a method of bacterial identification, and use a drug susceptibility test (test time is about 24 hours) to confirm whether the bacteria are resistant to specific antibiotics.

Methods for MRSA identification is to use polymerase chain reaction or gene sequencing targeting the drug resistance genes to determine whether the strain is drug resistant. However, compared with the MALDI-TOF MS identification method, the gene sequencing method requires higher costs, high training requirements for operators, and relatively long time consumption. Therefore, MALDI-TOF MS has emerged as a potential tool for microbial identification and diagnosis in the clinical microbial identification. There have been many prior disclosures using MALDI-TOF MS as the related technology for MRSA identification. In the past, related technology disclosures were mainly performed on known strains (including the mass spectrum of drug-resistant or drug-sensitive *Staphylococcus aureus*) to analyze and compare to find novel biomarkers to identify MRSA. In addition, analyzing the mass spectra obtained through a mass spectrometer analysis by commercial software can directly identify bacterial species and further to predict whether they are drug-resistant strains. However, this prediction result is often different from the actual clinical test results obtained by clinical patients. Therefore, more accurate biomarkers for the diagnosis of MRSA are urgently needed for the correct diagnosis of clinical patient infections and the determination of antibiotic treatment.

SUMMARY OF THE INVENTION

The present invention relates to a method for identifying methicillin-resistant *Staphylococcus aureus*, comprising: (a) providing a bacterial sample; (b) depositing the bacterial sample on a matrix-assisted laser desorption ionization time-of-flight mass spectrometry (MALDI-TOF) mass spectrometer target plate; (c) acquiring a MALDI-TOF mass spectrum of the bacterial sample; and (d) determining the presence of a mass signal at m/z of 6580-6600 in the MALDI-TOF mass spectrum, and identifying the bacterial sample which comprises methicillin-resistant *Staphylococcus aureus*.

In one aspect, the present invention relates to a peptide for identifying methicillin-resistant *Staphylococcus aureus* consists of SEQ NO ID:5.

In another aspect, the present invention relates to a method for identifying methicillin-resistant *Staphylococcus aureus*, comprising: (a) providing a bacterial sample; and (b) determining the presence of a peptide which consists of SEQ NO ID:5, and identifying the bacterial sample which comprises methicillin-resistant *Staphylococcus aureus*.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3B shows the m/z range from 2850 to 2940. FIG. 3C shows the m/z range from 2970 to 3290. The peaks of P3, P4 and P5 are significant differences between the mass spectra of MRSA and MSSA. The m/z of P3 is about 2880, the m/z of P4 is 3005 and the m/z of P5 is about 3050.

FIG. 11A shows peptide mapping of the peptide fragments of MRSA64 after being hydrolyzed by pancreatic protein and Glu-C hydrolase. FIG. 11C shows the MASCOT search result of protein identification for the peptide fragment with a m/z of 6593.2 in MRSA64.

FIG. 12C shows the MASCOT search result of protein identification for the peptide fragment with a m/z of 6550 in MSSA6.

DETAILED DESCRIPTION OF THE INVENTION

Figures 1A, 1B:
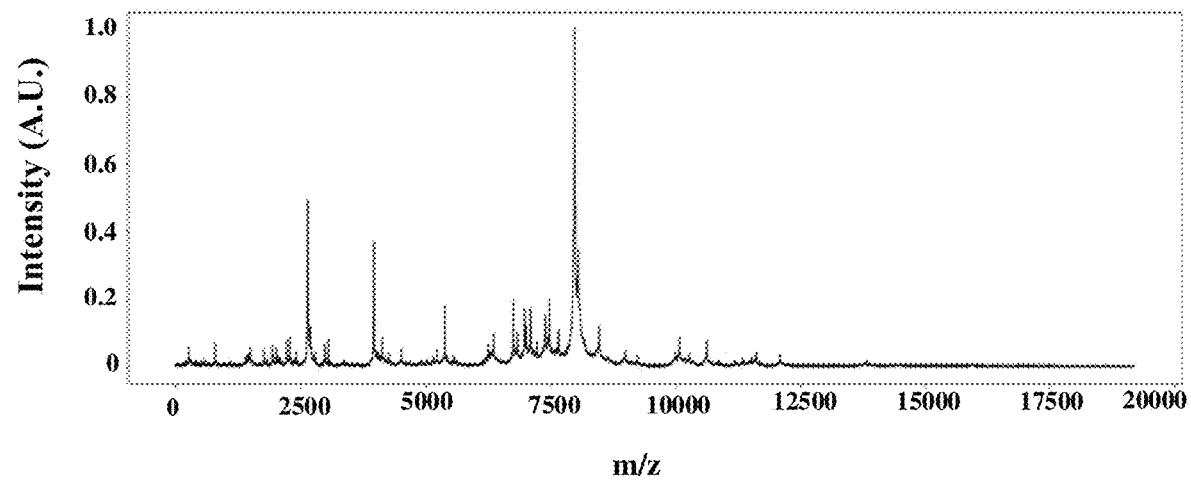
FIG. 1A shows a schematic diagram of the mass spectrum obtained by MALDI-TOF MS analysis of microorganisms (not the content of this implementation), X-axis is mass-to-charge ratio (m/z), Y-axis represents signal intensity of the ions. (Arbitrary unit, au).
FIG. 1B shows the content of the report of the microbial drug susceptibility test inspection, as a comprehensive situation to determine the antibiotics of the bacteria.

Not otherwise defined herein, otherwise the scientific and technical terms used in this disclosure should have the meanings commonly understood and used by those of ordinary skill in the art. In addition, unless the context requires otherwise, it should be understood that singular terms shall include the same plural form, and plural terms shall include the singular. Specifically, the singular forms "a" and "an" as used herein and in the claims include plural forms unless the context clearly dictates otherwise.

Although the numerical ranges and parameters that illustrate the wide range of the present invention are approximate values, the numerical values set forth in the specific embodiments are reported as accurately as possible. However, any value contains certain errors, and these errors must be caused by the standard deviations in the various test measurements. Also, as used herein, the term "about" refers to within an acceptable standard error of the mean when considered by one of ordinary skill in the art. Except in the operating/working examples, or unless expressly stated otherwise, all numerical ranges, quantities, values, and percentages disclosed herein should be understood to be described by the term "about" in all cases. Therefore, unless otherwise indicated, the numerical parameters set forth in the present disclosure and the appended claims are approximate values that can be changed as desired. At the very least, each numerical parameter should at least be interpreted based on the number of significant figures reported and by applying ordinary rounding techniques.

The present invention relates to a method for identifying methicillin-resistant *Staphylococcus aureus*, comprising: (a) providing a bacterial sample; (b) depositing the bacterial sample on a matrix-assisted laser desorption ionization time-of-flight mass spectrometry (MALDI-TOF) mass spectrometer target plate; (c) acquiring a MALDI-TOF mass spectrum of the bacterial sample; and (d) determining the presence of a mass signal at m/z of 6580-6600 in the MALDI-TOF mass spectrum, and identifying the bacterial sample which comprises methicillin-resistant *Staphylococcus aureus*.

In one embodiment, the bacterial sample is a body fluid or a tissue, preferably the bacterial sample is a body fluid.

In another embodiment, the body fluid is selected form the group consisting of blood, serum, saliva, digestive juice, tears, sweat, urine, and combinations thereof.

In one embodiment, the mass signal at m/z of 6580-6600 comprises a peptide having amino acid sequence of SEQ ID NO: 5.

In another embodiment, the mass signal comprises a first mass signal at m/z of 6580-6600, and a second mass signal at m/z of 3030-3050.

In another embodiment, the mass signal comprises a first mass signal at m/z of 6580-6600, a second mass signal at m/z of 3030-3050 and a third mass signal at m/z of 3760-3770.

In another embodiment, the mass signal comprises a first mass signal at m/z of 6580-6600, a second mass signal at m/z of 3030-3050, a third mass signal at m/z of 3760-3770, and a fourth mass signal at m/z of 6540-6560.

In another embodiment, the signal intensity of the second mass signal obtained from methicillin-resistant *Staphylococcus aureus* is higher than those from methicillin-sensitive *Staphylococcus aureus*.

In another embodiment, the signal intensity of the third mass signal obtained from methicillin-resistant *Staphylococcus aureus* is lower than those from methicillin-sensitive *Staphylococcus aureus*.

In one aspect, the present invention relates to a peptide for identifying methicillin-resistant *Staphylococcus aureus* consists of SEQ NO ID:5.

In another aspect, the present invention relates to a method for identifying methicillin-resistant *Staphylococcus aureus*, comprising: (a) providing a bacterial sample; and (b) determining the presence of a peptide which consists of SEQ NO ID:5, and identifying the bacterial sample which comprises methicillin-resistant *Staphylococcus aureus*.

In one embodiment, the bacterial sample is a body fluid or a tissue, preferably the bacterial sample is a body fluid. preferably the bacterial sample is a body fluid.

In another embodiment, the body fluid is selected form the group consisting of blood, serum, saliva, digestive juice, tears, sweat, urine, and combinations thereof.

In another embodiment, the peptide is detected by a method selected from the group consisting of matrix-assisted laser desorption ionization time-of-flight mass spectrometry (MALDI-TOF MS) analysis, liquid chromatography electrospray ionization mass spectrometry (LC-ESI-MS) analysis, liquid chromatography tandem mass spectrometry (LC-MS/MS) analysis, gas chromatography mass spectrometry (GS/MS) analysis, high performance liquid chromatography (HPLC), ultra-high performance liquid chromatography (UPLC), and combinations of thereof.

EXAMPLES

The present invention can be implemented in many different forms and should not be construed as being limited to the examples set forth herein. The described examples are not limited to the scope of the invention described in the claims.

Example 1. Establishment and Analysis of Database

The source of clinical specimens:
The verification data was the retrospective microbiological test data (IRB number: CMUH109-REC3-098) collected by China Medical University Hospital (IRB number: CMUH109-REC3-098), including MSSA (Class0) and MRSA (Class1). MALDI-TOF analysis data can be obtained by comparing the mass spectra of MRSA or MSSA with those already established in commercial analysis software. The profile of mass spectra of each strain and the m/z of the strain were retained during each clinical test. The record (FIG. 1A), combined with the subsequent antibiotic sensitivity test results (FIG. 1B) can be established as a database for distinguishing MRSA or MSSA for further analysis the mass spectra differentiation.

Operation of mass spectrometer (Bruker MALDI Biotyper) for microbial identification:

1. Preparation of specimen
(1) Preparation method for direct smearing of bacteria
Use a clean toothpick to dip the fresh microbial colony to be identified (the incubation time was between 24 and 48 hours), and directly apply a thin layer of the specimen on the clean MALDI sample plate. After air-drying, add 1 µL of 70% formic acid (FA) to the bacteria on the MALDI sample pan, and dry at room temperature. Next, add 1 µL of α-cyano-4-hydroxycinnamic acid (CHCA) matrix solution to the bacteria on the MALDI sample plate, and air dry at room temperature. The air-dried samples are applied to the MALDI-TOF mass spectrometer for analysis and bacterial identification.

(2) Preparation method of bacteria first extracted with formic acid (FA)
Pick a single colony or 5-10 mg of bacterial pellet and place it in a 1.5 mL microcentrifuge tube containing 300 µL of pure water. After the bacteria are fully dispersed and homogenized in the water, add 900 µL of absolute alcohol and mix well. It can be stored at −18° C. for up to 6 months, and at room temperature for several days. Then, centrifuge at 15,000 g for 2 minutes, after removing the supernatant, perform a second centrifugation at 15,000 g for a second time for 2 minutes, and then remove the remaining supernatant as much as possible and air dry for a few of minutes. Next, add 25 µL of 70% formic acid (the volume of 70% formic acid can be adjusted according to the amount of bacteria, the range is usually 1-80 µL). Then use a micropipette to repeatedly suck and release or use shaking to fully disperse and homogenize the bacteria. After fully mixing, add CHCA with the same volume as 70% FA solution and shake to make it evenly mixed. After mixing, centrifuge at the highest speed of 15000 g for 2 minutes, take 1 µL of the supernatant, place it on the MALDI sample plate, and air-dry at room temperature. Add 1 µL of HCCA matrix solution to the air-dried sample. After the sample is air-dried, it can be analyzed and identified by the MALDI-TOF mass spectrometer.

(3) After the laser pulse is applied to the sample, the mass spectra of MRSA or MSSA is obtained. In linear mode, the detected mass range is 1000 to 10000 mass-to-charge ratio, and in reflection mode, the detected mass range is 1000 to 4000 mass-to-charge ratio.

2. Analyze with microflex LT instrument software
3. Check the identification results from the MALDI Biotyper Realtime Classification (RTC)

Results: FIG. 1A is a schematic diagram of the mass spectrum obtained by MALDI-TOF MS analysis of microorganisms (not the content of this implementation). The peaks shown in the mass spectra are mainly used to distinguish MRSA and MSSA. FIG. 1B is the report of the drug susceptibility test of microorganisms as the comprehensive status of determining the bacterial species to antibiotics. The content contains the name of the bacteria, the results of the drug susceptibility test (S: sensitive/effective, R: resistant/ineffective, MIC: minimum inhibitory concentration), Gram stain classification, and bacterial type. First, obtain the average intensity from the mass spectra data judged as MSSA or MRSA from the database. Compare and analyze the mass spectra with the average intensity of MSSA and MRSA. The peaks with obvious differences are marked with arrows in the figures (P1-P9).

Figures 2, 2A:
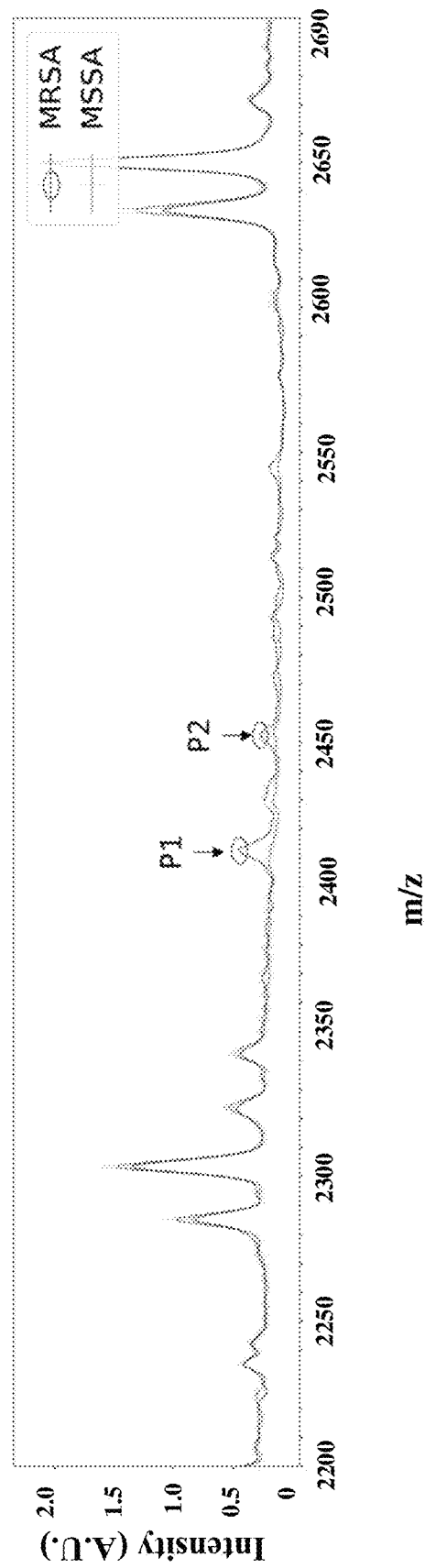
FIG. 2 shows the mass spectra of MRSA and MSSA specimens subjected to MALDI-TOF MS.
FIG. 2A shows the mass-to-charge ratio (m/z) range from 2200 to 2690.
Figures 2, 2B:
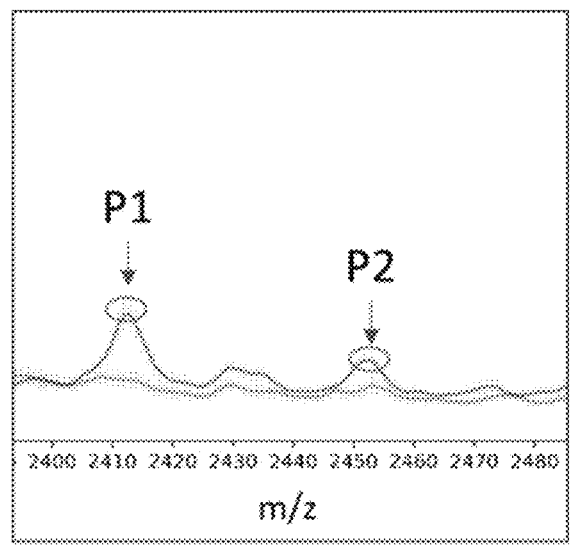
FIG. 2B shows the m/z range from 2400 to 2480. The peaks of P1 and P2 are significant differences between the mass spectra of MRSA and MSSA. The m/z of P1 is about 2412-2413, and the m/z of P2 is about 2450.
Figures 3, 3A:
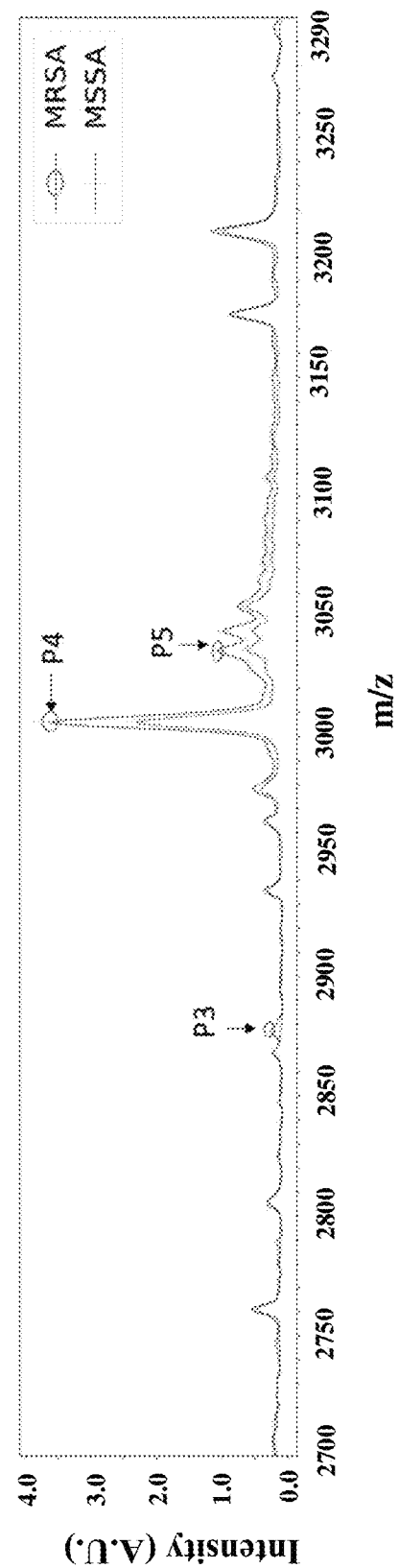
FIG. 3 shows the mass spectra of MRSA and MSSA specimens subjected to MALDI-TOF MS.
FIG. 3A shows the m/z range from 2700-3290.
Figures 4, 4A:
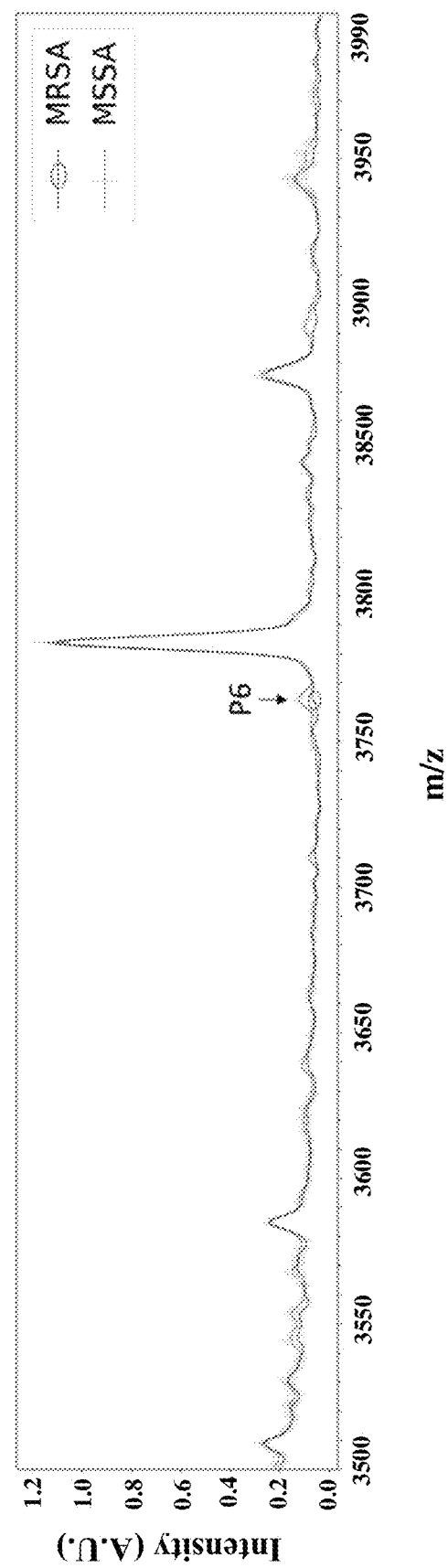
FIG. 4 shows the mass spectra of MRSA and MSSA specimens subjected to MALDI-TOF MS.
FIG. 4A shows the m/z range from 3500 to 3990.
Figures 4, 4B:
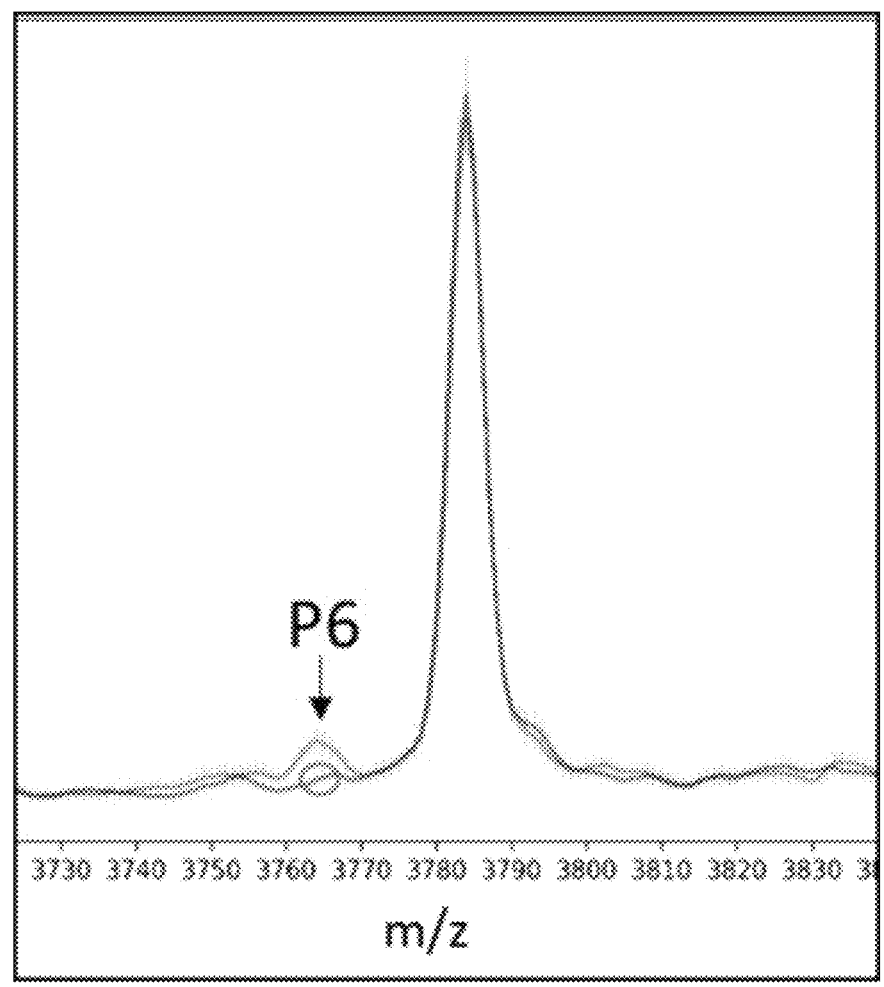
FIG. 4B shows the m/z range from 3730 to 3830. The peak of P6 is significant difference between the mass spectra of MRSA and MSSA. The m/z of P6 is about 3736-3763.
Figures 5, 5A:
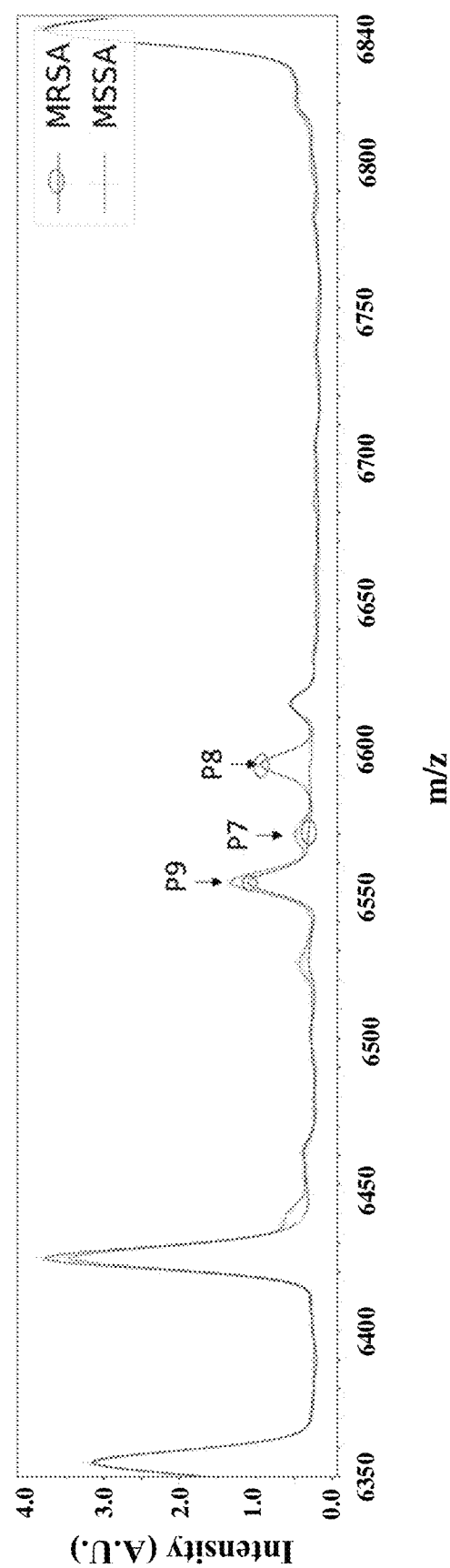
FIG. 5 shows the mass spectra of MRSA and MSSA specimens subjected to MALDI-TOF MS.
FIG. 5A shows the m/z range from 6350 to 6840.
Figures 5, 5B:
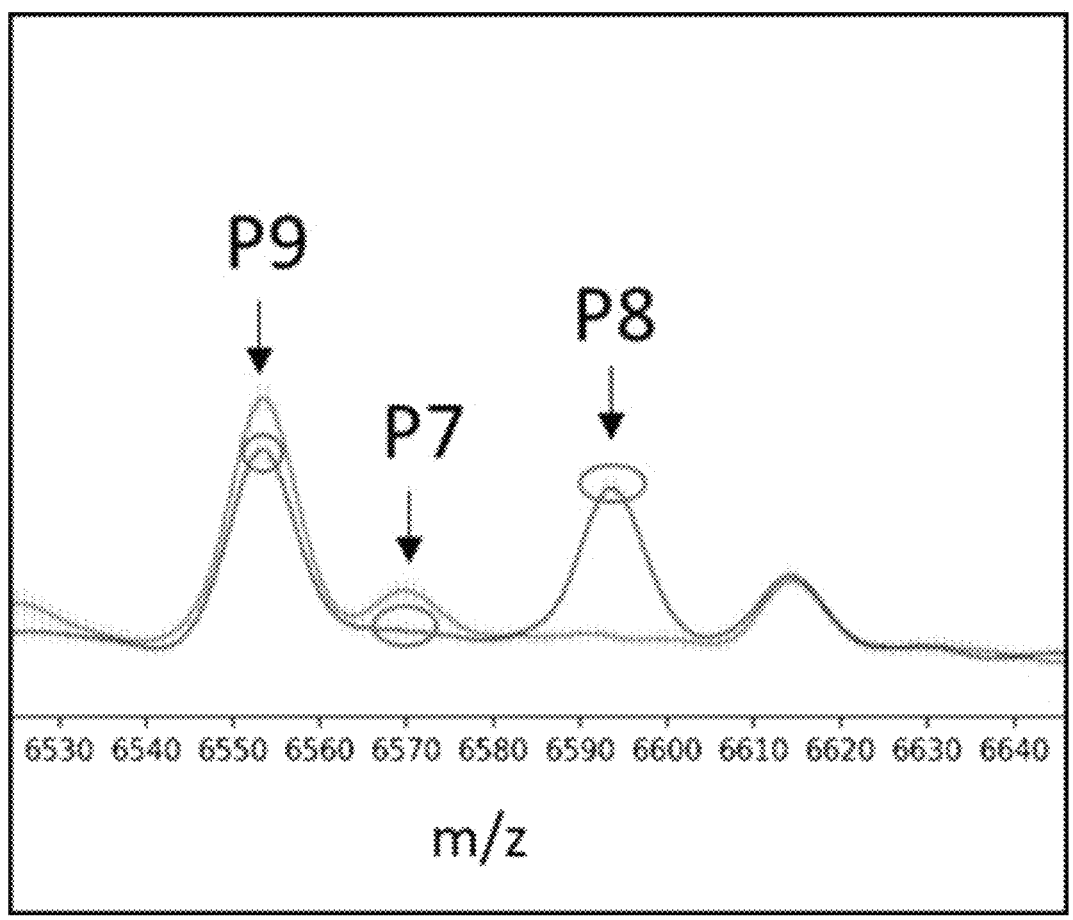
FIG. 5B shows the m/z range from 6530 to 6640. The peaks of P7, P8 and P9 are significant differences between the mass spectra of MRSA and MSSA. The m/z of P7 is about 6570, the m/z of P8 is 6590-6593, and the m/z of P9 is about 6540 to 6560.

The results are detailed as follows: FIG. 2A shows the mass-to-charge ratio (m/z) range from 2200 to 2690, and FIG. 2B shows the m/z range from 2400-2480, where the m/z of P1 is about 2412-2413, and the m/z of P2 is about 2450. FIG. 3A shows the m/z range from 2700 to 3290, FIG. 3B shows the m/z range from 2850 to 2940, and FIG. 3C shows the m/z range from 2970 to 3070, where the m/z of P3 is about 2880, the m/z of P4 is about 3005 and the m/z of P5 is about 3035-3050. FIG. 4A shows the m/z range from 3500 to 3990, FIG. 4B shows the m/z range from 3730 to 3830, where the m/z of P6 is about 3762-3763. FIG. 5A shows the m/z range from 6350 to 6840, FIG. 5B shows the m/z range from 6530 to 6640, where the m/z of P7 is about 6570, the m/z of P8 is about 6590-6593, and the m/z of P9 is about 6540 to 6560.

Example 2: Identify Important Biomarkers of MRSA and MSSA and their Combinations In order to find the important biomarker combination used to identify MRSA, the biological characteristics of different mass-to-charge ratios are found by averaging all the samples of all MRSA and MSSA in FIG. 2 to FIG. 5. Hence, the present invention further use machine learning and deep learning algorithms to learn and search for important features.

Figure 7:
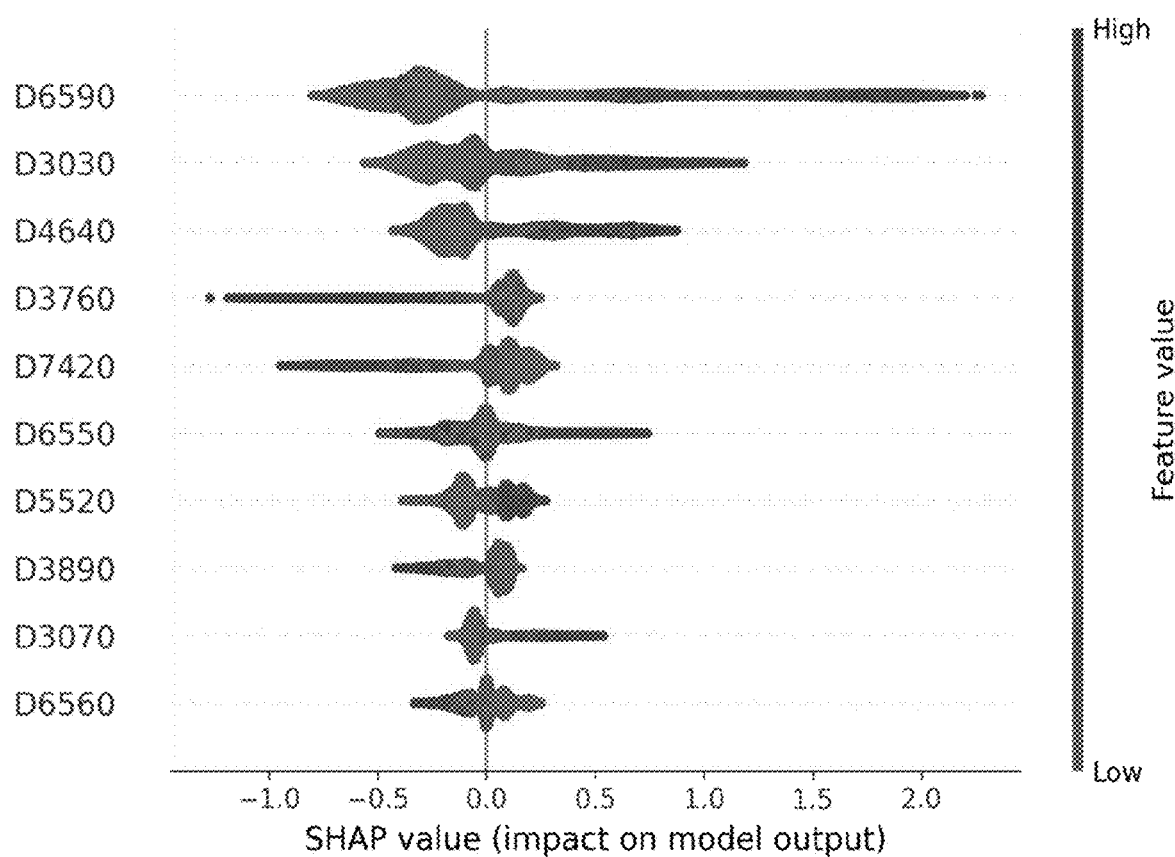
FIG. 7 shows a summary graph of the results of the SHAP (SHapley Additive exPlanation) analysis. The X axis is the SHAP value, which is mainly used to judge the influence of a feature on the output of a model. The right Y axis shows the feature value, and the left Y axis quality the mass-to-charge ratio (m/z) is analyzed as each feature. The SHAP value is mainly used to evaluate the importance of each feature.

SHAP (SHapley Additive exPlanation) values are mainly used to evaluate the importance of features. Since the peptide fragments will cross a range of charge mass, averaging every 10 Da will be more effective to observe the difference in charge mass range. Using the SHAP summary graph in FIG. 7 shows that the m/z of 6590-6600 (D6590) is the most important, followed by 3030-3040 (D3030), 4640-4650 (D4640), 3760-3770 (D3760) and 7420-7430 (D7420). The feature value represents the value of the quality interval. Taking the m/z of 6590-6600 as an example (D6590), when the average mass of the interval is larger (that is, the higher the characteristic value), the higher probability of drug-resistant *Staphylococcus aureus*(MRSA) is determined. In addition, the m/z of 7420-7430 shows that the smaller the average mass of the area (that is, the lower the characteristic value), the higher probability of MRSA is determined. Therefore, from a biological point of view, when the signal intensity of peptides with the m/z of 6590, 3030, and 4640 increase, and the signal intensity of peptides with the m/z of 3760 and 7420 decrease, the higher possibility of MRSA is determined.

Figure 6:
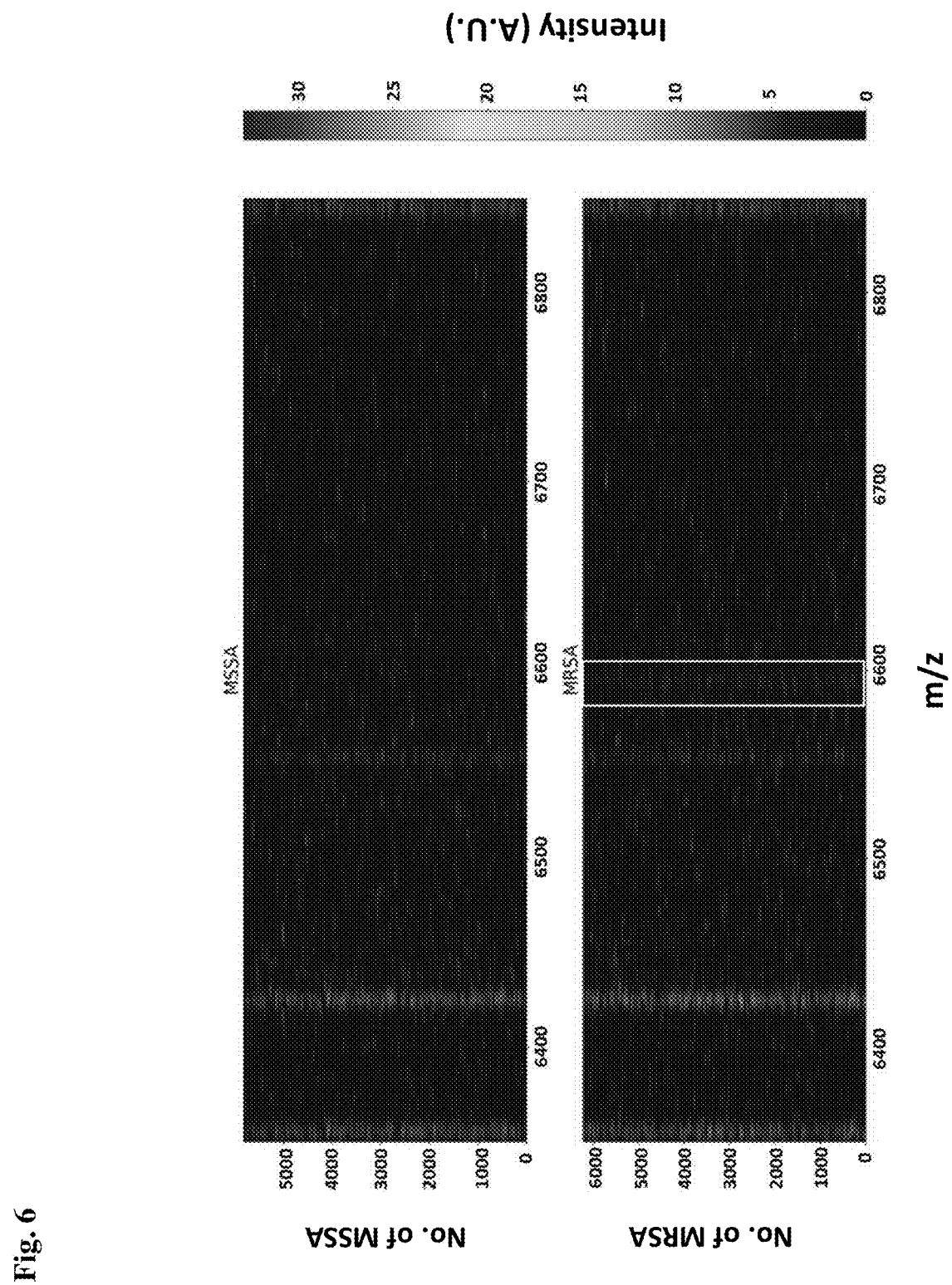
FIG. 6 shows a virtual gel (pseudo-gel) diagram of a mass spectra. X axis is the mass-to-mass ratio (m/z) and Y axis is showed as the bacteria strain No. of MRSA or MSSA. The color gradation on the right Y axis shows signal strength detected by the mass spectrometer. The detected signal showing the m/z is between 6590 to 6600 (white box) mainly appears in the MRSA graph (lower panel), but not in the MSSA graph (upper panel).

From the results of FIG. 5 and FIG. 7, it can be concluded that the most important mass-to-charge ratio for identifying MRSA is 6591±5 m/z. In order to further confirm that the predicted result is consistent with the performance of the actual sample, a virtual gel chart demonstration of the mass spectrum was performed. In FIG. 6, X axis is the mass-to-charge ratio, the left Y axis is the strain number of MRSA or MSSA, and the right Y axis is the color gradation of the signal intensity detected by the mass spectrometer. The result shows that the signal with a mass-to-charge ratio of 6590-6600 mainly appears in the MRSA diagram (FIG. 6, lower, the signal shown in the white box below), but not in the MSSA (FIG. 6, upper). Therefore, a peptide with a charge-to-mass ratio of 6591±5 m/z can be used as an important biomarker to identify MRSA.

Figure 8:
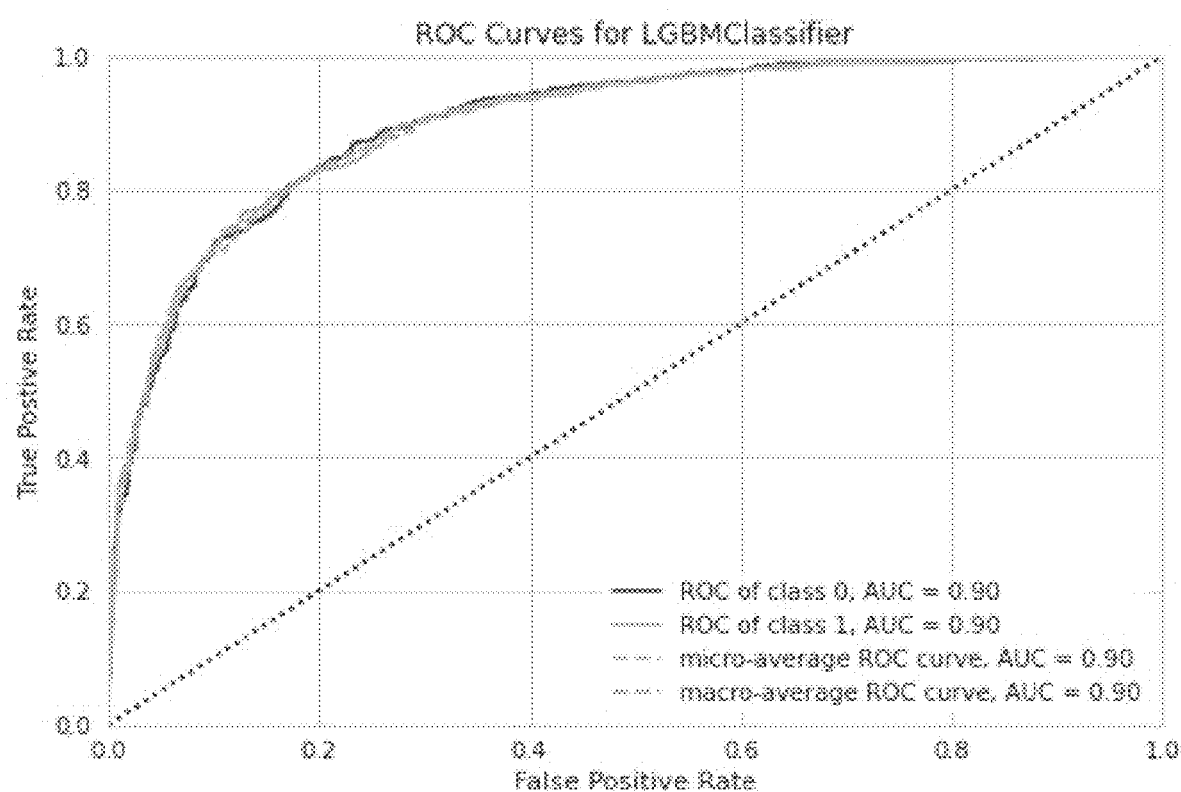
FIG. 8 shows the ROC curve of the classification of MRSA from MSSA using the four mass-to-charge ratios as a feature combination.

Furthermore, a receiver operating characteristic curve (ROC) curve was created by combining the 4 types of features, and the AUC (area under the curve) value was obtained for MRSA resistance classification prediction. In general, if the AUC is between 0.7 and 0.9, it is a method with high accuracy. The AUC value is often used to evaluate the diagnostic value of the test. The higher the value, the higher the diagnostic value. The results in FIG. 8 show the combination of the biological characteristics of the four mass-to-charge ratios, including m/z of 3033±3, 3762±3, 6551±5 and 6591±5. The average AUC under the ROC curve obtained by the analysis of the machine learning model LGBMClassifier is 0.9. Class 1 is the MRSA group. Class 0 is the MSSA group. The macro average ROC curve first calculates the value of each type of statistical index and then calculates the arithmetic average of all the classes. The micro-average ROC curve uses statistics for each instance in the data set without classification to establish a global confusion matrix, and then calculate its average. However, the two indicators (macro- and micro-average ROC curves) are exactly the same when there are only two categories. In addition, commercial software (ClinProTools) was used to predict the drug resistance of MRSA bacteria with a single mass-to-charge ratio. After comparing the mass spectra of MRSA and MSSA, a single peak (m/z) was selected for verification. The data showed that the AUC value of a single m/z obtained by ROC analysis was lower than the four feature combinations.

Example 3: Identification of Peptide Sequences Used to Identify Important Biomarkers of MRSA and MSSA Protein analysis was used to identify peptide fragments that can be used to distinguish MRSA from MSSA. First, the samples of MRSA (No. MRSA64) and MSSA (No. MSSA4) were sorted through a liquid chromatography column C4 column fractionation and the obtained fractions were analyzed by MALDI-TOF MS to generate mass spectrum. Next, isolate the peaks which was be further analyzed, and then perform protein hydrolysis. The hydrolyzed protein fragments were identified by liquid chromatography-tandem mass spectrometry (LC-MS/MS). Each MS/MS spectrum was processed by DataAnalysis 4.4 software (Bruker) to generate ion mass list. The identification of each peptide was completed by entering the quality list in the Mascot 2.6 server, and further searching and confirming according to its protein database. In addition, amino acid sequence analysis and database alignment were used to confirm the protein identity of the analysis.

Figure 9:
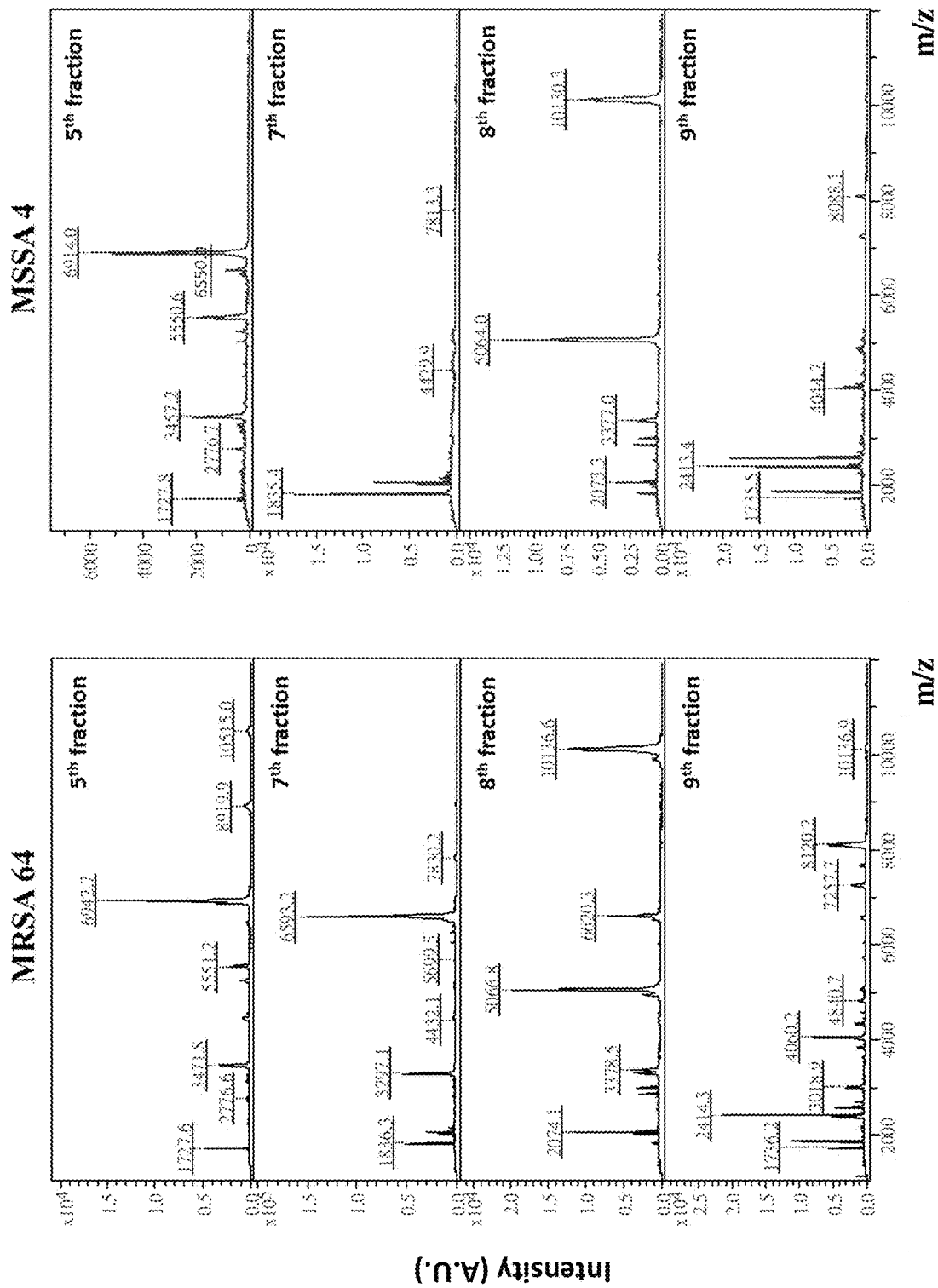
FIG. 9 shows the mass spectra of MRSA64 and MSSA4 samples after fractionation with C4 column for mass spectrometry detection, including the mass spectra of the $5^{th}$, $7^{th}$, $8^{th}$ and $9^{th}$ fraction. X axis shows the spectrum signal and the m/z range from 0 to 12000.
Figure 10:
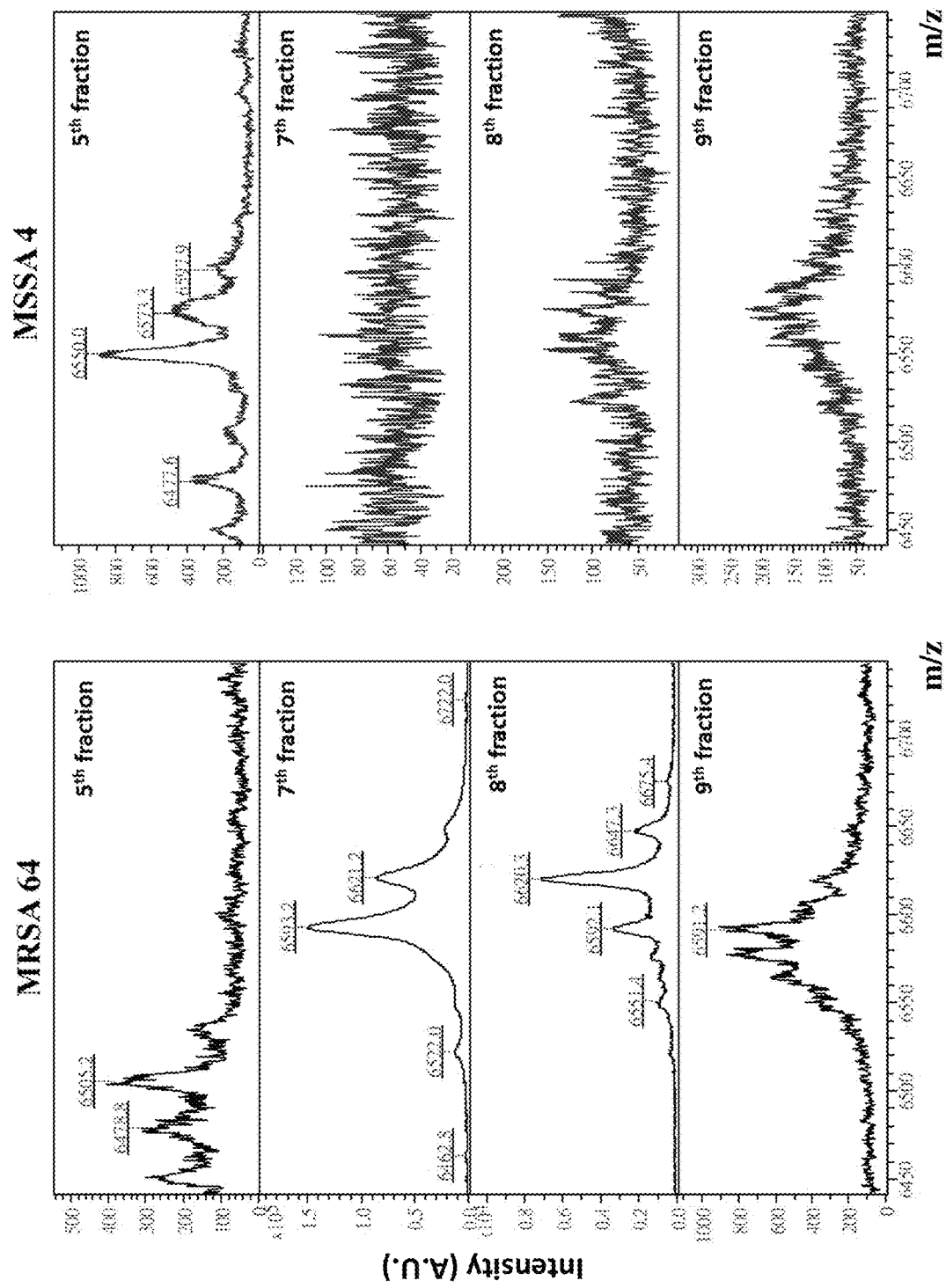
FIG. 10 shows the mass spectra of MRSA64 and MSSA4 samples after fractionation with C4 column for mass spectrometry detection. The mass spectra including the mass spectra of the $5^{th}$, $7^{th}$, $8^{th}$, and $9^{th}$ fraction. X axis shows the spectrum signal and the m/z range from 6400 to 6800.

FIG. 9 and FIG. 10 show samples of MRSA64 and MSSA4 subjected to liquid chromatography (C4 column fractionation) and MALDI-TOF MS analysis. The mass spectra show the $5^{th}$, $7^{th}$, $8^{th}$, and $9^{th}$ fraction after fractionation, respectively. The FIG. 9 shows the mass spectrum signal with a m/z of 1000-12000, and FIG. 10 shows the mass spectrum signal with a m/z of 6440-6750. Comparing the mass spectra of MRSA64 and MSSA4, a signal with a m/z of 6550 in the $5^{th}$ fraction was found in MSSA4, but not in MRSA64. On the contrary, a signal with a m/z of 6593.2 was increased in the $7^{th}$ fraction of MRSA64, but not in MSSA4 (FIG. 10).

Figures 11, 11B:
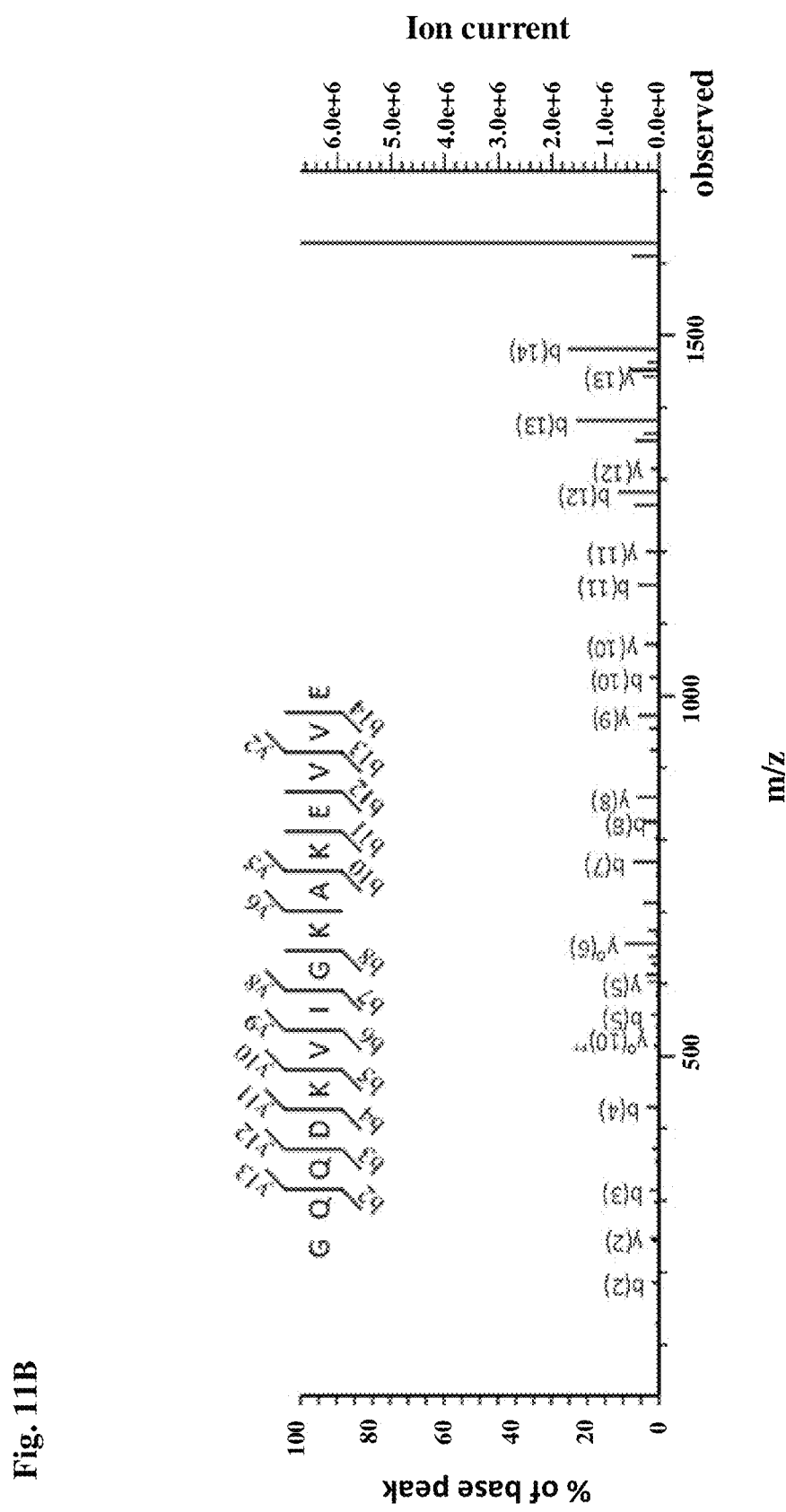
FIG. 11 shows the results of protein identification and analysis of the peptide fragment with a m/z of 6593.2 in MRSA64.
FIG. 11B shows the peptide identification spectra of the peptide fragment with a m/z of 6593.2 in MRSA64.
Figures 12, 12A:
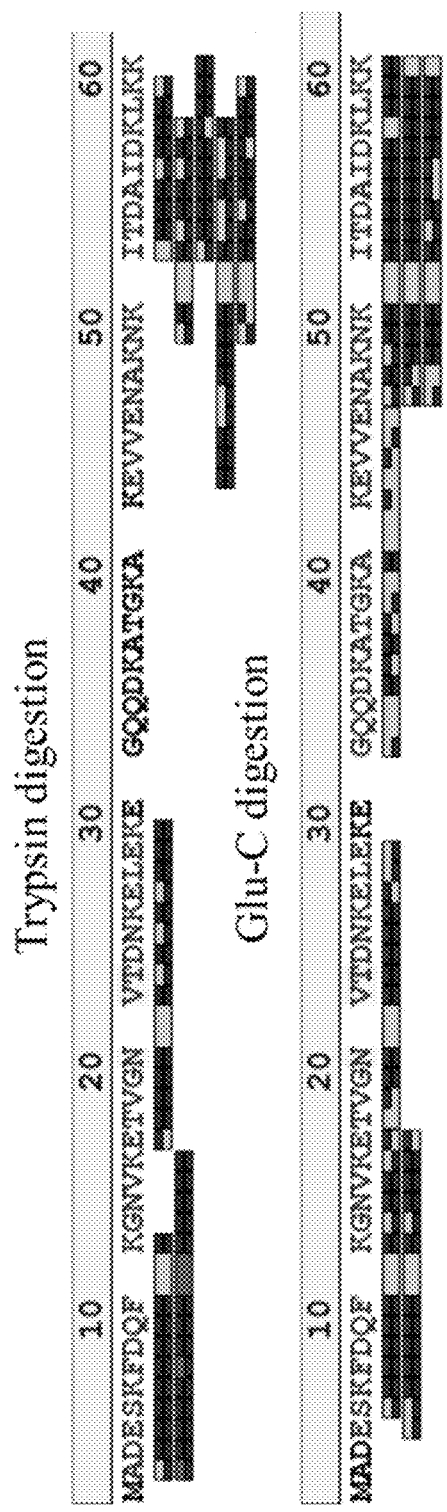
FIG. 12 shows the results of protein identification and analysis of the peptide fragment with a m/z of 6550 in MSSA6.
FIG. 12A shows peptide mapping of the peptide fragments of MSSA6 after being hydrolyzed by pancreatic protein and Glu-C hydrolase.

FIG. 11 shows the results of protein identification and analysis of peptide fragments in MRSA64 samples with a m/z of 6593.2. FIG. 12 shows the identification and analysis results of peptide fragments with a m/z of 6550 in MSSA4 samples. FIG. 11A and FIG. 12A show the peptide fragments of MRSA64 and MSSA4 respectively after being hydrolyzed by pancreatic protein and Glu-C hydrolase for peptide mapping.

The amino acid sequences of the peptide fragments with a m/z of 6593.2 in MRSA64 and a m/z of 6550 in MSSA4 are listed in Table 1 and Table 2, respectively.

TABLE 1

Protein identification information of MRSA64 samples:

| Sample | column fractionation | Peak (m/z) |
|---|---|---|
| MRSA64 | 7th fraction | 6593.2 |

Fragments identified by trypsin digestion of proteins (indicated in bold and underlined):
MADESKFDQF KGNVKETVGN VTDNKELEKE GQQDKVIGKA KEVVENAKNK ITDAIDKLKK (SEQ NO ID: 1)

Fragments identified by Glu-C protease digestion of proteins (indicated in bold and underlined):
MADESKFDQF KGNVKETVGN VTDNKELEKE GQQDKVIGKA KEVVENAKNK ITDAIDKLKK (SEQ NO ID: 2)

Protein identification results:
Q5HFD7 (Y1680_STAAC) UPF0337 protein SACOL168 (SACOL1680) Or Q2FGA1 (Y1582_STAA3) UPF0337 protein SAUSA300_1582 (SAUSA300_1582) protein (average neutral mass is 6722.53 m/z), which degrades the first amino acid Met, so the mass detected by mass spectrometry is 6591.48 m/z.

TABLE 2

Protein identification information of MSSA4 samples:

| Sample | C4 column fractionation | Peak (m/z) |
|---|---|---|
| MSSA4 | 5th fraction | 6551 |

Fragments identified by trypsin digestion of proteins (indicated in bold and underlined):
MADESKFDQF KGNVKETVGN VTDNKELEKE GQQDKATGKA KEVVENAKNK ITDAIDKLKK (SEQ NO ID: 3)

Fragments identified by Glu-C protease digestion of proteins (indicated in bold and underlined):
MADESKFDQF KGNVKETVGN VTDNKELEKE GQQDKATGKA KEVVENAKNK ITDAIDKLKK (SEQ NO ID: 4)

Protein identification results:
Q7A593 (Y1452_STAAN) UPF0337 protein SA1452 protein (average neutral mass is 6682.46 m/z) degrades the first amino acid Met, so the mass spectrum detection mass is 6551.48 m/z.

The peak signal detected in the 7th fraction of MRSA64 was 6593.2, and the protein was identified as Q5HFD7 (Y1680_STAAC) UPF0337 protein SACOL168 (SACOL1680) or Q2FGA1 (Y1582_STAA3) UPF0337 protein USA SAUSA300_1582 (SA300_1582). The average neutral mass of the protein is 6722.53 m/z. When the first amino acid Met was degraded, the mass detected by mass spectrometry was 6591.48 m/z, which was 6722.5 m/z-131m/z [149 Da-18 Da (dehydrated upon binding)=131 Da]. In addition, the peak signal detected in the 5th fraction of MSSA4 was 6551, and the protein was identified as Q7A593 (Y1452_STAAN) UPF0337 protein SA1452, which the average neutral mass of the protein (average neutral mass) was 6682.46 m/z. When the first amino acid Met was degraded, the mass detected by mass spectrometry was 6551.48 m/z, which was 6682.46 m/z-131 m/z [149 Da-18 Da (dehydrated when combined)=131 Da].

Figures 12, 12B:
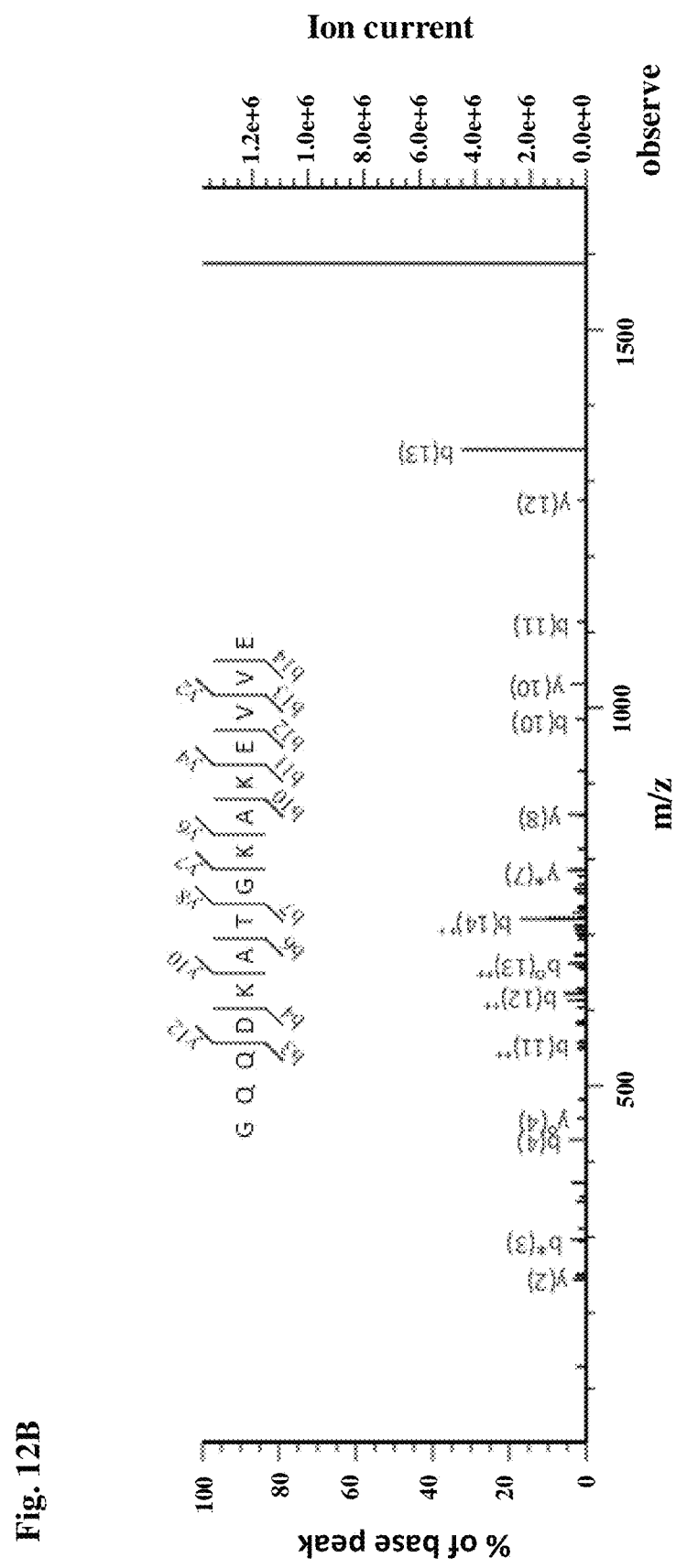
FIG. 12B shows the peptide identification spectra of the peptide fragment with a m/z of 6550 in MSSA6.

From the results of FIG. 11B and FIG. 12B, the difference of the sequence between MRSA and MSSA is that MRSA is GQQDKVIGKAKEVVE (SEQ NO ID: 5) and MSSA is GQQDKATGKAKEVVE (SEQ NO ID: 6). Therefore, the peptide sequence GQQDKVIGKAKEVVE (SEQ NO ID: 5) can be used as a peptide biomarker to distinguish MRAS and MSSA.

In the present invention, the peptide markers listed in Table 3 that have important mass-to-charge ratios in MRSA and MSSA are used to predict whether a sample contains MRSA, and therefore can be used as a clinically accurate and rapid judgment standard.

TABLE 3

Important mass-to-charge ratios used to distinguish MRSA and MSSA

| Predictive ranking | First range | Second range | Peak change |
|---|---|---|---|
| 1st m/z | 6580-6600 | 6586-6600 | The peak signal increases in the MRSA sample, but there is no signal in the MSSA sample. |
| 2nd m/z | 3030-3050 | 3033-3034 | The peak signal increases in the MRSA sample. Also, the signal can be detected in MSSA sample. |
| 3rd m/z | 3760-3770 | 3762-3763 | The peak signal decreases in the MRSA sample. But, the signal can be detected in MSSA sample. |
| 4th m/z | 6540-6560 | 6543-6546 | The peak signal decreases in the MRSA sample. But, the signal can be detected in MSSA sample. |

What is claimed is:

1. A method for identifying methicillin-resistant *Staphylococcus aureus*, comprising:
   (a) providing a bacterial sample;
   (b) depositing the bacterial sample on a matrix-assisted laser desorption ionization time-of-flight mass spectrometry (MALDI-TOF) mass spectrometer target plate;
   (c) acquiring a MALDI-TOF mass spectrum of the bacterial sample; and
   (d) determining the presence of a first mass signal at m/z of 6580-6600 and a second mass signal at m/z of 3030-3040 in the MALDI-TOF mass spectrum, and identifying the bacterial sample which comprises methicillin-resistant *S. aureus*.

2. The method of claim 1, wherein the bacterial sample is a body fluid or a tissue.

3. The method of claim 2, wherein the body fluid is selected from the group consisting of blood, serum, saliva, digestive juice, tears, sweat, urine, and combinations thereof.

4. The method of claim 1, wherein the first mass signal at m/z of 6580-6600 comprises a peptide having amino acid sequence of SEQ ID NO: 5.

5. The method of claim 1, wherein the mass signal further comprises a third mass signal at m/z of 3760-3770.

6. The method of claim 5, wherein the mass signal further comprises a fourth mass signal at m/z of 6540-6560.

7. The method of claim 1, wherein the signal intensity of the second mass signal obtained from methicillin-resistant *S. aureus* is higher than those from methicillin-sensitive *S. aureus*.

8. The method of claim 5, wherein the signal intensity of the third mass signal obtained from methicillin-resistant *S. aureus* is lower than that from methicillin-sensitive *S. aureus*.

* * * * *